US007049071B2

(12) United States Patent
Walmsley et al.

(10) Patent No.: US 7,049,071 B2
(45) Date of Patent: May 23, 2006

(54) DETECTION OF DNA DAMAGING AGENTS

(75) Inventors: Richard Maurice Walmsley, Manchester (GB); Wolf-Dietrich Heyer, Davis, CA (US)

(73) Assignee: University of Manchester Institute of Science and Technology, Manchester (GB)

( * ) Notice: Subject to any disclaimer, the term of this patent is extended or adjusted under 35 U.S.C. 154(b) by 354 days.

(21) Appl. No.: 10/244,292

(22) Filed: Sep. 16, 2002

(65) Prior Publication Data

US 2003/0049690 A1    Mar. 13, 2003

Related U.S. Application Data

(63) Continuation of application No. 09/381,989, filed as application No. PCT/GB98/00786 on Mar. 27, 1998, now Pat. No. 6,489,099.

(30) Foreign Application Priority Data

Mar. 27, 1997  (GB)  .................................... 9706414

(51) Int. Cl.
  *C12Q 1/68*  (2006.01)
  *C12Q 1/02*  (2006.01)
(52) U.S. Cl. ............................. 435/6; 435/29
(58) Field of Classification Search ............... 536/24.1; 435/320.1, 325, 419, 243, 6
  See application file for complete search history.

(56) References Cited

FOREIGN PATENT DOCUMENTS

| EP | 0163491 | 12/1985 |
|---|---|---|
| WO | WO 9417208 A | 8/1994 |
| WO | WO 9507463 A | 3/1995 |

OTHER PUBLICATIONS

Filatov et al, The Journal of Biological Chemistry, Sep. 27, 1996, vol. 271, No. 39, pp. 23698-23704.*
C.M. James, et al., "DNA Sequence Analysis of a 35 Kb Segment from *Saccharomyces cerevisiae* Chromosome VII reveals 19 Open Reading Frames Including RAD54, ACE1/ CUP2, PMR1, RCK1, AMS1, and CAL1/CDC43.," Yeas, vol. 11, 1995, pp. 1413-1419.
J.D. Plautz, et al., "Green Fluorescent Protein and its Derivatives as Versatile Markers for Gene Expression in Living *Drosophila melanogaster*, Plant and Mammalian Cells," GENE, vol. 73, 1996, pp. 83-87.
B.P. Cormack, et al., "Yeast-Enhanced Green Fluorescent Protein (yEGFP): a Reporter of Gene Expression in *Candida albicans*," Microbiology, vol. 143, Feb. 1997, pp. 303-311.
A. Wach, et al., "New Heterlogous Modules for Classical or PCR-Based Gene Disruptions in *Saccharomyces cerevisiae*," Yeast, vol. 10, 1994, pp. 1793-1808.
S.J. Elledge, et al., "Identification of the DNA Damage-Responsive Element of RNR2 and Evidence that Four Distinct Cellular Factors Bind it," Molecular and Cellular Biology, vol. 9, No. 12, 1989, pp. 5373-5386.
G.M. Cole, et al., "Failure to Induce a DNA Repair Gene, RAD54, in *Saccharomyces cerevisiae* Does not Affect DNA Repair or Recombination Phenotypes," vol. 9, No. 8, 1989, pp. 3314-3322.
D.W. Russel, et al., "Structure of *Saccharomyces cerevisiae* HO Gene and Analysis of its Upstream Regulatory Region," Molecular and Cellular Biology, vol. 6, No. 12, 1986, pp. 4281-4294.
W.J. Welch, "How Cells Respond to Stress," Scientific American vol. 5, May 1993, pp. 34-41.
R.M. Walmsley, et al., "Green Fluorescent Protein as a Reporter for the DNA Damage-Induced Gene RAD54 in *Saccharomyces cerevisiae*," Yeast, vol. 13, Dec. 1997, pp. 1535-1545.

* cited by examiner

*Primary Examiner*—Terry McKelvey
(74) *Attorney, Agent, or Firm*—Hogan & Hartson, L.L.P.

(57) ABSTRACT

Recombinant DNA molecules comprising a regulatory element that activates gene expression in response to DNA damage operatively linked to a DNA sequence that encodes a light emitting reporter protein, recombinant vectors containing such DNA molecules and cells containing the DNA molecules or recombinant vectors. A method of detecting for the presence of an agent that causes or potentiates DNA damage is also disclosed which involves subjecting the above-described cells to a putative DNA damaging agent and monitoring the expression of the light emitting reporter protein from the cell.

10 Claims, 7 Drawing Sheets

SEQUENCE LISTING

<160> NUMBER OF SEQ ID NOS: 9

<210> SEQ ID NO 1
<211> LENGTH: 1729
<212> TYPE: DNA
<213> ORGANISM: Saccharomyces cerevisiae

<400> SEQUENCE: 1

```
gacatacgat gacctcaatg atttagatta tgtgttgcac ttttatagac ctaccaaaaa        60
tccagtgcgt acactaatac tttcataaag atacctgaaa caataaccag aaagatcggc       120
aaaaaaattt tttttctttg ccgagatcac aaacctacta tgacgaaaaa gcttgaagtt       180
tagatgagta aggaaaatac aagtgacgct tttatatggt gcaaggaaca aaaactaaaa       240
acaacaaggc aaatgtggat ctgtcatgta tggcaacgac agcaggatgg ctcacaaaaa       300
aagacaaaaa aaactaaggc aaaagaacaa agctcctctc ctgctcaaga aacgtattgt       360
tgaaaaacca ccgtcgtaag aaagtttttc tgtgacctat aatggtttaa aatcggccca       420
ttttttttcc ctcttttgtg gtccagtctt tctcatactc gagggaaatt cgacacaaac       480
agcggagaag tgtggctaaa ccggcaagtg cctgcaagat ccacagaact aaccgcacga       540
actggcggtc agaaaagagc ctgttccgga agagagaaa cagagaaacg atcatgatgg       600
gaaagcgggg attcggcgaa gaacgagact ggaaagggaa aaagagaaat actggtggaa       660
gtattcggac ctttggcgaa gtccgaaccc ttgaaaccca aagatgatcg atgattcatt       720
tttcaatgcg ctacggttcc tgccgctcgt gggaaccca cgcaaaacat attattcgct       780
tctctctgct gacaactccg gtttacgtta taccgtatta ggatcactat aagggttcct       840
tcgggaggag ggggagggg aagaatgtac atcgtcataa ggcctttatg gtgtgaagtg       900
ggttttgcgt ggaaaattcg ttttcaatga tatagagccc acgcatatac gtacatacta       960
gtggccaaaa gcgtggggtg ggcggacaaa gctacactgg taaatacag gattctatga      1020
acaataacaa caaccagctc acgttgctga acagccgagg tcagccgatg caaccgaggt      1080
ttccaaagta gcatttctgt gctagctatg tctgtaggtt tacatttaat ggtgcgtggt      1140
tccagcttca tgtgcttgca tgtgatgtcc tgcagatggt aagaagattc tgaaagccgc      1200
gctaggagaa aaatattctg ctcgaagatc tgtcctctta agtagaaagc gtgaaattgt      1260
tgcgttcttg cattactact caacgcgtac gcaaatgcgt ctactgcacc tgcatgataa      1320
agcttatgta tcaaaaattt aacatcttga aaatacacaa gtggtgcaaa gatgtgtcac      1380
gttctggacc tgagtggtgc catgtatgct atttaacatg caaaggggaa gacccttccg      1440
ccttactgca ataataaaaa gtattttacg cgttacccaa tatagcaaag tttcgcgcaa      1500
aaaaaaaaat aaaaaacaat tacaaacaaa aagaaaaaaa aggaaataat agaagatcta      1560
```

```
actgaagcga aggccaaaac tcttctcact tgacgtaata gccgatacaa aatctagagc    1620
agcaactttt ctctttcttc actaaagctg ctacgaaagt atagaaaaat caaacgctca    1680
gaacttagct ctatttcaag gtaccatata tatttcctta taactgatg                1729

<210> SEQ ID NO 2
<211> LENGTH: 31
<212> TYPE: DNA
<213> ORGANISM: saccharomyces cerevisiae

<400> SEQUENCE: 2
cctccggatc cgacatacga tgacctcaat g                                     31

<210> SEQ ID NO 3
<211> LENGTH: 44
<212> TYPE: DNA
<213> ORGANISM: saccharomyces cerevisiae

<400> SEQUENCE: 3
cctccgttaa ttaacatcag ttataaggaa atatatatgg tacc                       44

<210> SEQ ID NO 4
<211> LENGTH: 5902
<212> TYPE: DNA
<213> ORGANISM: saccharomyces cerevisiae

<400> SEQUENCE: 4
gaacgcggcc gccagctgaa gcttcgtacg ctgcaggtcg acggatcccc gggttaatta      60
acagtaaagg agaagaactt ttcactggag ttgtcccaat tcttgttgaa ttagatggtg     120
atgttaatgg gcacaaattt tctgtcagtg gagagggtga aggtgatgca acatacggaa     180
aacttaccct taaatttatt tgcactactg gaaaactacc tgttccatgg ccaacacttg     240
tcactacttt ctcttatggt gttcaatgct tttcaagata cccagatcat atgaaacggc     300 atgactttt caagagtgcc atgcccgaag ttatgtaca ggaaagaact atattttca       360 aagatgacgg gaactacaag acacgtgctg aagtcaagtt tgaaggtgat acccttgtta     420
atagaatcga gttaaaaggt attgatttta agaagatgg aaacattctt ggacacaaat     480
tggaatacaa ctataactca cacaatgtat acatcatggc agacaaacaa aagaatggaa     540
tcaaagttaa cttcaaaatt agacacaaca ttgaagatgg aagcgttcaa ctagcagacc     600
attatcaaca aaatactcca attggcgatg gccctgtcct tttaccagac aaccattacc     660
tgtccacaca atctgccctt tcgaaagatc ccaacgaaaa gagagaccac atggtccttc     720
ttgagtttgt aacagctgct gggattacac atggcatgga tgaactatac aaatagggcg     780
cgccacttct aaataagcga atttcttatg atttatgatt tttattatta ataagttat     840 aaaaaaaata agtgtataca aattttaaag tgactcttag gttttaaaac gaaaattctt     900
attcttgagt aactctttcc tgtaggtcag gttgctttct caggtatagt atgaggtcgc     960
tcttattgac cacacctcta ccggcagatc cgctagggat aacagggtaa tatagatctg    1020
cccgccggga aggcgaaccc gatcggatgc atcctctctg ctgccatgat gctgaagttg    1080
tcgttgaaca tggttgctgc cggcgaggcg gtcgagcagg cagtgcagga ggtgttggac    1140
tcgggagtca gaacgggcga cctgctcggc tcgagctcca cttcggaggt tggcgacgcc    1200
attgcgcttg cagttaagga agccttgcgc aggcaatccg cagctggtct gagctagcct    1260
cgaggaccct tctctttaga ctattctact cttatgcacg taaaaaattc taggaaatat    1320
```

-continued

```
gtattaacta ggagtaaaat aaccggctag tggcattcat atagccgtct gtttacatct    1380
acatcacaca tttcgagtgt atatctcgca acgttggcgt taaataggca gtcaatggcc    1440
cgaccattct atggtgttta ggtcgatgcc atctttgtac agcttgcctc gtccccgccg    1500
ggtcacccgg ccagcgacat ggaggcccag aatacccctcc ttgacagtct tgacgtgcgc   1560
agctcagggg catgatgtga ctgtcgcccg tacatttagc ccatacatcc ccatgtataa    1620
tcatttgcat ccatacattt tgatggccgc acggcgcgaa gcaaaaatta cggctcctcg    1680
ctgcagacct gcgagcaggg aaacgctccc ctcacagacg cgttgaattg tccccacgcc    1740
gcgcccctgt agagaaatat aaaaggttag gatttgccac tgaggttctt ctttcatata    1800
cttccttttta aaatcttgct aggatacagt tctcacatca catccgaaca taaacaacca   1860
tgggtaagga aaagactcac gtttcgaggc cgcgattaaa ttccaacatg gatgctgatt    1920
tatatgggta taaatgggct cgcgataatg tcgggcaatc aggtgcgaca atctatcgat    1980
tgtatgggaa gcccgatgcg ccagagttgt ttctgaaaca tggcaaaggt agcgttgcca    2040
atgatgttac agatgagatg gtcagactaa actggctgac ggaatttatg cctcttccga    2100
ccatcaagca ttttatccgt actcctgatg atgcatggtt actcaccact gcgatccccg    2160
gcaaaacagc attccaggta ttagaagaat atcctgattc aggtgaaaat attgttgatg    2220
cgctggcagt gttcctgcgc cggttgcatt cgattcctgt ttgtaattgt ccttttaaca    2280
gcgatcgcgt atttcgtctc gctcaggcgc aatcacgaat gaataacggt ttggttgatg    2340
cgagtgattt tgatgacgag cgtaatggct ggcctgttga acaagtctgg aaagaaatgc    2400
ataagctttt gccattctca ccggattcag tcgtcactca tggtgatttc tcacttgata    2460
accttatttt tgacgagggg aaattaatag gttgtattga tgttggacga gtcggaatcg    2520
cagaccgata ccaggatctt gccatcctat ggaactgcct cggtgagttt tctccttcat    2580
tacagaaacg ctttttcaa aaatatggta ttgataatcc tgatatgaat aaattgcagt     2640
ttcatttgat gctcgatgag ttttttctaat cagtactgac aataaaaaga ttcttgtttt    2700
caagaacttg tcatttgtat agttttttta tattgtagtt gttctatttt aatcaaatgt    2760
tagcgtgatt tatattttt ttcgcctcga catcatctgc ccagatgcga agttaagtgc      2820
gcagaaagta atatcatgcg tcaatcgtat gtgaatgctg gtcgctatac tgctgtcgat    2880
tcgatactaa cgccgccatc cagtgtcgac tagggttgct gccatcggcc tcgctcgcgt    2940
ctttgccgga tagcaagagc gcctttggcc tctacgagcc ctgccacggc tctgcgcccg    3000
atctgcccgc cgggaaggcg aacccgatcg gatgcatcct ctctgctgcc atgatgctga    3060
agttgtcgtt gaacatggtt gctgccggcg aggcggtcga gcaggcagtg caggaggtgt    3120
tggactcggg agtcagaacg ggcgacctgc tcggctcgag ctccacttcg gaggttggcg    3180
acgccattgc gcttgcagtt aaggaagcct tgcgcaggca atccgcagct ggtctgagct    3240
agcctcgagg acccttctct ttagactatt ctactcttat gcacgtaaaa aattctagga    3300
aatatgtatt aactaggagt aaaataaccg gctagtggca ttcatatagc cgtctgttta    3360
catctacatc acacatttcg agtgtatatc tcgcaacgtt ggcgttaaat aggcagtcaa    3420
tggcccgacc attctatggt gtttaggtcg atgccatctt tgtacgttta acgagctcg     3480
aattcatcga tgatatcaga tccactagtg gcctatgcgg ccgcgatct gccggtctcc    3540
ctatagtgag tcgtattaat ttcgataagc caggttaacc tgcattaatg aatcggccaa    3600
cgcgcgggga gaggcggttt gcgtattggg cgctcttccg cttcctcgct cactgactcg    3660
ctgcgctcgg tcgttcggct gcggcgagcg gtatcagctc actcaaaggc ggtaatacgg    3720
```

```
ttatccacag aatcagggga taacgcagga agaacatgt gagcaaaagg ccagcaaaag   3780
gccaggaacc gtaaaaaggc cgcgttgctg cgttttttcc ataggctccg cccccctgac   3840
gagcatcaca aaaatcgacg ctcaagtcag aggtggcgaa acccgacagg actataaaga   3900
taccaggcgt ttccccctgg aagctccctc gtgcgctctc ctgttccgac cctgccgctt   3960
accggatacc tgtccgcctt tctcccttcg ggaagcgtgg cgctttctca atgctcacgc   4020
tgtaggtatc tcagttcggt gtaggtcgtt cgctccaagc tgggctgtgt gcacgaaccc   4080
cccgttcagc ccgaccgctg cgccttatcc ggtaactatc gtcttgagtc caacccggta   4140
agacacgact tatcgccact ggcagcagcc actggtaaca ggattagcag agcgaggtat   4200
gtaggcggtg ctacagagtt cttgaagtgg tggcctaact acggctacac tagaaggaca   4260
gtatttggta tctgcgctct gctgaagcca gttaccttcg gaaaagagt tggtagctct   4320 tgatccggca acaaaccac cgctggtagc ggtggttttt tgtttgcaa gcagcagatt   4380 acgcgcagaa aaaaggatc tcaagaagat cctttgatct tttctacggg gtctgacgct   4440
cagtggaacg aaaactcacg ttaagggatt ttggtcatga gattatcaaa aaggatcttc   4500
acctagatcc ttttaaatta aaaatgaagt tttaaatcaa tctaaagtat atatgagtaa   4560
acttggtctg acagttacca atgcttaatc agtgaggcac ctatctcagc gatctgtcta   4620
tttcgttcat ccatagttgc ctgactcccc gtcgtgtaga taactacgat acgggagggc   4680
ttaccatctg gccccagtgc tgcaatgata ccgcgagacc cacgctcacc ggctccagat   4740
ttatcagcaa taaaccagcc agccggaagg gccgagcgca gaagtggtcc tgcaacttta   4800
tccgcctcca tccagtctat taattgttgc cgggaagcta gagtaagtag ttcgccagtt   4860
aatagtttgc gcaacgttgt tgccattgct acaggcatcg tggtgtcacg ctcgtcgttt   4920
ggtatggctt cattcagctc cggttcccaa cgatcaaggc gagttacatg atcccccatg   4980
ttgtgcaaaa aagcggttag ctccttcggt cctccgatcg ttgtcagaag taagttggcc   5040
gcagtgttat cactcatggt tatggcagca ctgcataatt ctcttactgt catgccatcc   5100
gtaagatgct tttctgtgac tggtgagtac tcaaccaagt cattctgaga atagtgtatg   5160
cggcgaccga gttgctcttg cccggcgtca atacgggata taccgcgcc acatagcaga   5220 actttaaaag tgctcatcat tggaaaacgt tcttcgggc gaaaactctc aaggatctta   5280
ccgctgttga gatccagttc gatgtaaccc actcgtgcac ccaactgatc ttcagcatct   5340
tttactttca ccagcgtttc tgggtgagca aaaacaggaa ggcaaaatgc cgcaaaaaag   5400
ggaataaggg cgacacggaa atgttgaata ctcatactct tcctttttca atattattga   5460
agcatttatc agggttattg tctcatgagc ggatacatat ttgaatgtat ttagaaaaat   5520
aaacaaatag gggttccgcg cacatttccc cgaaaagtgc cacctgacgt ctaagaaacc   5580
attattatca tgacattaac ctataaaaat aggcgtatca cgaggccctt tcgtctcgcg   5640
cgtttcggtg atgacggtga aaacctctga cacatgcagc tcccggagac ggtcacagct   5700
tgtctgtaag cggatgccgg gagcagacaa gcccgtcagg gcgcgtcagc gggtgttggc   5760
gggtgtcggg gctggcttaa ctatgcggca tcagagcaga ttgtactgag agtgcaccat   5820
atggacatat tgtcgttaga acgcggctac aattaataca taaccttatg tatcatacac   5880
atacgattta ggtgacacta ta                                            5902
```

<210> SEQ ID NO 5
<211> LENGTH: 909
<212> TYPE: DNA

<213> ORGANISM: saccharomyces cerevisiae

<400> SEQUENCE: 5

```
tttaaaatgc tttctgaaaa cacgactatt ctgatggcta acggtgaaat taaagacatc      60
gcaaacgtca cggctaactc ttacgttatg tgcgcagatg gctccgctgc ccgcgtcata     120
aatgtcacac agggctatca gaaaatctat aatatacagc aaaaaaccaa acacagagct     180
tttgaaggtg aacctggtag gttagatccc aggcgtagaa cagtttatca gcgtcttgca     240
ttacaatgta ctgcaggtca taaattgtca gtcagggtcc ctaccaaacc actgttggaa     300
aaaagtggta gaaatgccac caaatataaa gtgagatgga gaaatctgca gcaatgtcag     360
acgcttgatg gtaggataat aataattcca aaaaccatc ataagacatt cccaatgaca     420
gttgaaggtg agtttgccgc aaaacgcttc atagaagaaa tggagcgctc taaggagaa     480
tatttcaact ttgacattga agttagagat ttggattatc ttgatgctca attgagaatt     540
tctagctgca taagatttgg tccagtactc gcaggaaatg gtgttttatc taaatttctc     600
actggacgta gtgaccttgt aactcctgct gtaaaaagta tggcttggat gcttggtctg     660
tggttaggtg acagtacaac aaaagagcca gaaatctcag tagatagctt ggatcctaag     720
ctaatggaga gtttaagaga aaatgcgaaa atctgggtc tctaccttac ggtttgtgac     780
gatcacgttc cgctacgtgc caaacatgta aggcttcatt atggagatgg tccagatgaa     840
aacaggaaga caaggaattt gaggaaaaat aatccattct ggaaagctgt cacaatttta     900
aagtttaaa                                                            909
```

<210> SEQ ID NO 6
<211> LENGTH: 756
<212> TYPE: DNA
<213> ORGANISM: saccharomyces cerevisiae

<400> SEQUENCE: 6

```
atgttaatta actctaaagg tgaagaatta ttcactggtg ttgtcccaat tttggttgaa      60
ttagatggtg atgttaatgg tcacaaattt tctgtctccg gtgaaggtga aggtgatgct     120
acttacggta aattgaccct aaaatttatt tgtactactg gtaaattgcc agttccatgg     180
ccaaccttag tcactacttt cggttatggt gttcaatgtt ttgcgagata cccagatcat     240
atgaaacaac atgacttttt caagtctgcc atgccagaag gttatgttca agaaagaact     300
atttttttca aagatgacgg taactacaag accagagctg aagtcaagtt tgaaggtgat     360
accttagtta atagaatcga attaaaaggt attgatttta agaagatgg taacattta     420
ggtcacaaat tggaatacaa ctataactct cacaatgttt acatcatggc tgacaaacaa     480
aagaatggta tcaaagttaa cttcaaaatt agacacaaca ttgaagatgg ttctgttcaa     540
ttagctgacc attatcaaca aaatactcca attggtgatg gtccagtctt gttaccagac     600
aaccattact tatccactca atctgcctta tccaaagatc aaacgaaaa gagagaccac     660
atggtcttgt tagaatttgt tactgctgct ggtattaccc atggtatgga tgaattgtac     720
aaataactgc agggcgcgcc acttctaaat aagcga                              756
```

<210> SEQ ID NO 7
<211> LENGTH: 20
<212> TYPE: DNA
<213> ORGANISM: Saccharomyces cerevisiae

<400> SEQUENCE: 7

```
gacatacgat gacctcaatg                                                  20
```

```
<210> SEQ ID NO 8
<211> LENGTH: 27
<212> TYPE: DNA
<213> ORGANISM: Saccharomyces cerevisiae

<400> SEQUENCE: 8
cagttataag gaaatatata tggtacc                                          27

<210> SEQ ID NO 9
<211> LENGTH: 17
<212> TYPE: DNA
<213> ORGANISM: Saccharomyces cerevisiae

<400> SEQUENCE: 9
cctccgttaa ttaacat                                                    17
```

DETECTION OF DNA DAMAGING AGENTS

This is a continuation of application Ser. No. 09/381,989 filed Jan. 12, 2000, now U.S. Pat. No. 6,489,099, which claims priority, under 35 U.S.C. 371, to PCT/GB98/00786 filed Mar. 27, 1998 identifying the United States as an elected country, which, in turn, is based on the United Kingdom Patent Application No. 9706414.1 filed Mar. 27, 1997, which applications are hereby incorporated by reference in their entirety.

The present invention relates to methods for detecting agents that cause or potentiate DNA damage and to molecules and transformed cells that may be usefully employed in such methods.

DNA damage is induced by a variety of agents such as ultraviolet light, X rays, free radicals, methylating agents and other mutagenic compounds. These agents may cause damage to the DNA that comprises the genetic code of an organism and cause mutations in genes. In microorganisms such mutations may lead to the evolution of new undesirable strains of the microorganism. For instance, antibiotic or herbicide resistant bacteria may arise. In animals these mutations can lead to carcinogenesis or may damage the gametes to give rise to congenital defects in offspring.

These DNA damaging agents may chemically modify the nucleotides that comprise DNA and may also break the phosphodiester bonds that link the nucleotides or disrupt association between bases (T-A or C-G). To counter the effect of these DNA damaging agents cells have evolved a number of mechanisms. For instance the SOS response in *E. coli* is a well characterised cellular response induced by DNA damage in which a series of proteins are expressed, including DNA repair enzymes, which repair the damaged DNA.

There are numerous circumstances when it is important to identify what agents may cause or potentiate DNA damage. It is particularly important to detect agents that cause DNA damage when assessing whether it is safe to expose a person to these agents. For instance a method of detecting these agents may be used as a mutagenesis assay for screening compounds that are candidate food additives, medicaments or cosmetics to assess whether or not the compound of interest induces DNA damage. Alternatively methods of detecting DNA damaging agents may be used to monitor for contamination of water supplies with pollutants that contain mutagenic compounds.

Various methods, such as the Ames Test, for determining the toxicity of an agent are known. More recent developments are disclosed in WO 95/00834 which relates to the use of a light emitting organism (particularly the bacterium *Photobacterium phosphoreum*) for measuring the toxicity of industrial effluents. WO 95/07463 discloses a gene construct formed from DNA encoding for Green Fluorescent Protein and DNA encoding for a regulatory element (such as a promoter induced by heavy metals) which may be used to detect pollution. However these developments do not disclose means of specifically monitoring for the presence of agents that may cause or potentiate DNA damage. Furthermore these known methods are not sensitive enough to detect agents that cause or potentiate DNA damage at low concentrations.

According to a first aspect of the present invention, there is provided a recombinant DNA molecule comprising a regulatory element that activates gene expression in response to DNA damage operatively linked to a DNA sequence that encodes a light emitting reporter protein.

According to a second aspect of the invention, there is provided a recombinant vector comprising a DNA molecule in accordance with the first aspect of the present invention and a DNA vector.

According to a third aspect of the invention, there is provided a cell containing a DNA molecule in accordance with the first aspect of the present invention or a recombinant vector in accordance with the second aspect of the present invention.

According to a fourth aspect of the present invention, there is provided a method of detecting for the presence of an agent that causes or potentiates DNA damage comprising subjecting a cell in accordance with the third aspect of the present invention to an agent and monitoring the expression of the light emitting reporter protein from the cell.

By "regulatory element" we mean a DNA sequence which regulates the transcription of a gene with which it is associated.

By "operatively linked" we mean that the regulatory element is able to induce the expression of the reporter protein.

By "reporter protein" we mean a protein which when expressed in response to the regulatory element of the DNA molecule of the invention is detectable by means of a suitable assay procedure.

The method of the fourth aspect of the invention is suitable for assessing whether or not an agent may cause DNA damage. It is particularly useful for detecting agents that cause DNA damage when assessing whether it is safe to expose a person to DNA damaging agents. For instance, the method may be used as a mutagenesis assay for screening whether or not known agents, such as candidate foodstuffs, medicaments or cosmetics, induce DNA damage. Alternatively the method of the invention may be used to monitor for contamination of water supplies with pollutants containing DNA damaging agents.

The method of the fourth aspect of the invention may equally be used for assessing whether an agent may potentiate DNA damage. For example, certain agents can cause DNA damage by inhibiting DNA repair (for instance by preventing expression of a repair protein) without directly inflicting DNA damage. These agents are often known as co-mutagens and include agents such as lead.

The regulatory element of the DNA molecule of the first aspect of the invention activates expression of the reporter protein when DNA damage occurs. Such regulatory elements ideally comprise a promoter sequence which induces RNA polymerase to bind to the DNA molecule and start transcribing the DNA encoding for the reporter protein. The regulatory element may also comprise other functional DNA sequences such as translation initiation sequences for ribosome binding or DNA sequences that bind transcription factors which promote gene expression following DNA damage. Regulatory elements may even code for proteins which act to dislodge inhibitors of transcription from the regulated gene and thereby increase transcription of that gene.

Preferred regulatory elements are DNA sequences that are associated in nature with the regulation of the expression of DNA repair proteins. For instance, the regulatory elements from genes such as RAD2, RAD6, RAD7, RAD18, RAD23, RAD51, RAD54, CDC7, CDC8, CDC9, MAG1, PHR1, DIN1, DDR48, RNR1, RNR2, RNR3 and UB14 from yeast may be used to make molecules according to the first aspect of the invention. There are also regulatory elements associated with inducible excision repair genes in Neurospora, inducible recombinational repair genes in Ustilago and UV inducible irradiation damage recovery pathway genes in mammalian cells which may be used.

A preferred regulatory element comprises the promoter and 5' regulatory sequences of the RAD54 repair gene. Such a regulatory element may be derived from yeast and particularly *Saccharomyces cerevisiae*. It is most preferred that the regulatory element comprises the promoter and 5' regulatory sequences of the RAD54 repair gene which correspond to the DNA sequence identified as SEQ ID NO 1 or a functional analogue or fragment thereof.

Another preferred regulatory element comprises the promoter and 5' regulatory sequences of the RNR2 gene. The RNR2 gene may be found on chromosome X of *Saccharomyces cerevisiae*. A preferred regulatory element may be derived from between co-ordinates 387100 and 398299 associated with the RNR2 gene on chromosome X as identified in the *Saccharomyces cerevisiae* genome database. The database may be accessed by the World Wide Web at many sites. For, example at http://genome-www.stanford.edu/.

The DNA sequences that encode a light emitting reporter protein may code for any light emitting protein, however it is preferred that the DNA sequences code for a protein that is fluorescent.

Preferred DNA sequences that encode a light emitting reporter protein code for Green Fluorescent Protein (GFP) and light emitting derivatives thereof. GFP is from the jelly fish *Aquorea victoria* and is able to absorb blue light and re-emits an easily detectable green light and is thus suitable as a reporter protein. GFP may be advantageously used as a reporter protein because its measurement is simple and reagent free and the protein is non-toxic.

Derivatives of GFP include DNA sequences encoding for polypeptide analogues or polypeptide fragments of GFP which are able to emit light. Many of these derivatives absorb and re-emit light at wavelengths different to GFP found endogenously in *Aquorea victoria*. For instance, preferred DNA molecules according to the first aspect of the invention have a DNA sequence that encodes the S65T derivative of GFP (in which serine 65 of GFP is replaced by a threonine). S65T GFP has the advantage that it is brighter than wild-type GFP (when excited at its longest-wavelength peak) and shows only slow photobleaching. Furthermore S65T GFP produces a good quantum yield of fluorescence and matches the output of argon ion lasers used in fluorescence activated cell sorters. Cells according to the third aspect of the invention which contain DNA molecules coding S65T GFP may be used according to the method of the fourth aspect of the invention and are particularly useful when light emission is measured from cell extracts (see below).

Another preferred DNA sequence encodes for a yeast enhanced GFP (YEGFP) such as the GFP derivative described by Cormack et al.(1997) (in Microbiology 143 p303–311). Such YEGFP has an amino acid sequence which is biased for usage in yeast. Thus YEGFP is particularly suitable for transforming cells according to the third aspect of the invention which are yeast. Furthermore we have found that light emitted from YEGFP in such yeast is even greater than that emitted by S65T derivatives. For example, light output from yeast strain FF18984 (also known as Y486) transformed with a DNA molecule coding YEGFP was double that output from FF18984 transformed with a DNA molecule coding S65T GFP. We have found that YEGFP is particularly suited for use in methods according to the fourth aspect of the invention which involve monitoring light emission from intact cells according to the third aspect of the invention (discussed in more detail below).

DNA molecules coding YEGFP are also useful because YEGFP is less heat sensitive than nascent GFP.

Most preferred DNA molecules according to the first aspect of the invention comprise a RAD54 regulatory element operatively linked to a DNA sequence that encodes a GFP or light emitting derivative thereof.

The DNA molecule may be contained within a suitable DNA vector to form a recombinant vector according to the second aspect of the present invention. The vector may for example be a plasmid, cosmid or phage. Such recombinant vectors are of great utility when replicating the DNA molecule of the first aspect of the invention. Furthermore recombinant vectors are highly useful for transforming cells with the DNA molecule and may also promote expression of the reporter protein.

The recombinant vectors will frequently include one or more selectable markers to enable selection of cells transfected with the DNA vector and, preferably, to enable selection of cells harbouring the recombinant vectors that incorporate the DNA molecule of the first aspect of the invention. Examples of such selectable markers include genes conferring resistance to kanamycin (or G148) and ampicillin. Selectable markers may include those which restore prototrophy, for example the yeast URA3 gene.

Recombinant vectors may be designed such that the vector will autonomously replicate in the cytosol of the cell. In this case, elements which induce DNA replication may be required in the recombinant vector. A suitable element is derived from the 2µ plasmid. Such replicating vectors can give rise to multiple copies of the DNA molecule in a transformant and are therefore useful when over-expression (and thereby increased light emission) of the reporter protein is required.

Alternatively the recombinant vector may be designed such that the vector and DNA molecule of the first aspect of the invention integrate into the genome of a cell. Such integration has the advantage of improved stability compared to replicative plasmids In this case DNA sequences which favour targeted integration (e.g. by homologous recombination) are desirable. For example, incorporation into the recombinant vector of fragments of the HO gene from chromosome IV of *Saccharomyces cerevisiae* favours targeted integration in *Saccharomyces cerevisiae* or cell-lines derived therefrom. It is preferred that the fragment of the HO gene has the sequence identified as SEQ ID No 5 or is a derivative thereof. It is also possible to insert multiple copies of integrating recombinant vectors into the genome. This will allow enable greater expression and increase the signal output further. For instance, the vectors may be targeted to chromosome XII using sequences from the ribosomal DNA array.

Preferably recombinant vectors may be formed from PFA vectors or derivatives thereof which are known to the art (see Wach el al. (1994) Yeast 10 p1793–1808).

Preferred DNA molecules according to the first aspect of the invention have a DNA sequence that encodes for a GFP or light emitting derivative thereof that is derived from these PFA vectors.

Preferred recombinant vectors are PFA KANMX3GFP-RAD54, pWDH443 and pWDH444 which are described in detail in the Example. The preferred DNA molecules of the first aspect of the present invention which comprise a RAD54 regulatory element operatively linked to a DNA sequence that codes for a GFP or light emitting derivative thereof may be derived from these most preferred recombinant vectors PFA KANMX3GFP-RAD54, pWDH443 or pWDH444.

Recombinant vector PFA KANMX3GFP-RAD54 comprises the vector of sequence listing SEQ ID NO 4 with the regulatory element of sequence listing SEQ ID NO 1 or a functional analogue or fragment thereof inserted between the Pac1 and BamH1 restriction enzyme sites of the vector of sequence listing SEQ ID NO 4.

Preferred recombinant vector pWDH443 comprises PFA KANMX3GFP-RAD54 with a fragment of the HO gene corresponding to SEQ ID NO 5 inserted at the unique BamH1 site of the KANMX3GFP-RAD54. pWDH443 comprises DNA coding for S65T GFP and is capable of integrating into the yeast genome.

Preferred recombinant vector pWDH444 comprises a fragment of the 2μ plasmid ligated with the large fragment generated from the BamH1 and Pme1 digestion of pWDH443. The fragment of the 2μ plasmid may correspond precisely to the large HindIII/BamH1 fragment released from the plasmid pRDK249, described in the Journal Biological Chemistry, Volume 266, p14049, FIG. 1 (1991) in the article by Johnson, A. W. and Kolodner, R. D. The DNA from the 2μ plasmid in pWDH444 allows this recombinant vector to autonomously replicate in the cytosol of a host cell and thereby allows the recombinant vector to be present in high copy numbers (which can be advantageous when over-expression of GFP and increased light emitting capability is desired).

Other preferred recombinant vectors are yEGFP-443 and yEGFP-444 (see FIGS. 11 and 12).

yEGFP-443 is derived from pWDH443 and comprises the large fragment of pWDH443 generated by Pac1 and Asc1 digestion with the Pac1 and Asc1 digestion product of SEQ ID NO 6 (which encodes a YEGFP) ligated into the said large fragment yEGFP-443 comprises DNA coding for YEGFP and is capable of integrating into the yeast genome.

yEGFP444 is derived from pWDH444 and comprises the large fragment of pWDH444 generated by Pac1 and Asc1 digestion with the Pac1 and Asc1 digestion product of SEQ ID NO 6 (which encodes a YEGFP) ligated into the said large fragment. The DNA from the 2μ plasmid in yEGFP-444 allows this recombinant vector to autonomously replicate in the cytosol of a host cell and thereby allows the recombinant vector to be present in high copy numbers (which can be advantageous when over-expression of GFP and increased light emitting capability is desired).

According to the third aspect of the invention the DNA molecule is incorporated within a cell. Such host cells may be prokaryotic or eukaryotic. Suitable host cells include bacteria, plant, yeasts, insect and mammalian cells. Preferred host cells are yeast cells such as *Saccharomyces cerevisiae*. Yeast are preferred because they can be easily manipulated like bacteria but are eukaryotic and therefore have DNA repair systems that are more closely related to humans than those of bacteria. Thus the use of such yeast in the method of the invention represents an improved method for detecting DNA damage relative to the Ames test. The Ames test uses bacteria (strains of *Salmonella typhimurium*) which when exposed to a putative DNA damaging agent may result in a genotoxicity result (positive or negative) which, because of the differences between prokaryotes and eukaryotes, would not necessarily be representative of the effects of such agents in eukaryotes such as humans.

Another benefit of using yeast cells as a host is that DNA repair systems are inducable in yeast unlike in humans where the repair systems are largely constitutive.

Preferred yeast cells include:

(i) Y485 in haploid form;

(ii) Y486 (also known as FF18984) in haploid form (iii) Y485/486 in diploid form;

(iv) FY73

(v) YLR030wα; and (vi) Y300.

These strains may all be found in national yeast strain collections.

The type of yeast strain used can influence the DNA damage response and we have found that light emission can vary greatly depending upon the yeast strain used. In this respect we have found that (i), (ii) and (iii) above are particularly useful strains for use according to the method of the invention.

Host cells used for expression of the protein encoded by the DNA molecule of the invention are ideally stably transformed, although the use of unstably transformed (transient) cells is not precluded.

Transformed cells according to the third aspect of the invention may be formed according to following procedures. PFA vectors may be used as suitable starting material from which DNA molecules of the first aspect of the invention and recombinant vectors of the second aspect of the invention may be formed. The known PFA vectors contain, or may be manipulated to contain, DNA encoding for GFP and derivatives thereof. Such vectors may be manipulated, by known molecular biology techniques, to insert a suitable regulatory element adjacent to the GFP coding sequence thus forming a DNA molecule of the first aspect of the invention which is contained within a recombinant vector according to the second aspect of the invention. For instance, pWDH443, pWDH444, yEGFP-443 and yEGFP-444 may be derived from such PFA vectors. The DNA molecule may be excised from the recombinant vector, or more preferably the DNA molecule contained within the recombinant vector may be used to transform a cell and thereby form a cell according to the third aspect of the invention. The cell is ideally a yeast cell (for instance one of the above described strains). Such transformed cells may be used according to the method of the fourth aspect of the invention to assess whether or not agents induce or potentiate DNA damage. GFP expression is induced in response to DNA damage and the light emitted by GFP may be easily measured using a fluorimeter as an index of the DNA damage caused. For instance, the light emitted by GFP at 511 nm (after excitation between 475 and 495 nm—e.g. 488 nm) in response to DNA damage, may be evaluated either in a suspension of a defined number of whole cells or from a defined amount of material released from cells following breakage.

Many known methods of detecting DNA damage (including the Ames Test and related methods) assay lasting DNA damage, as an endpoint, either in the form of misrepaired DNA (mutations and recombinations) or unrepaired damage in the form of fragmented DNA. However most DNA damage is repaired before such an endpoint can be measured and lasting DNA damage only occurs if the conditions are so severe that the repair mechanisms have been saturated. Preferred methods of the fourth aspect of the present invention are much more sensitive than these known methods because they detect repair activity (which we have found to be detectable when actual DNA damage is undetectable)

which prevents the above mentioned endpoint being reached. Therefore the method of the fourth aspect of the invention may be used to detect for the presence of DNA damaging agents or DNA damage potentiating agents at concentrations below the threshold for which actual DNA damage may be detected.

The method of the fourth aspect of the invention is particularly useful for detecting agents that induce DNA damage at low concentrations. The methods may be used to screen compounds, such as candidate medicaments, food additives or cosmetics, to assess whether it is safe to expose a living organism, particularly people, to such compounds.

Alternatively the methods of the fourth aspect of the invention may be employed to detect whether or not water supplies are contaminated by DNA damaging agents or agents that potentiate DNA damage. For instance, the methods may be used to monitor industrial effluents for the presence of pollutants that may lead to increased DNA damage in people or other organisms exposed to the pollution.

When the methods are used to detect whether or not water supplies are contaminated, the cells according to the third aspect of the invention are ideally unicellular organisms such as bacteria, algae, protoza and particularly yeast.

The expression of light emitting reporter protein may be monitored according to the method of the invention from cell extracts (in which case cells transformed with any of the above described recombinant DNA molecules and/or recombinant vectors may be used) or from samples containing intact, whole cells (in which case yEGFP-443 and yEGFP444 transformed yeast cells are preferably used).

There are several advantages associated with the use of whole cells. As there is no requirement to break open cells, the number of treatment steps is reduced. The production of extracts requires cell-harvesting, washing, breakage with glass beads and centrifugation to clear the extract. The reduction in treatment steps also reduces the risk of errors arising in handling and makes the method much faster. Furthermore cell density and light emission can be made simultaneously giving greater sensitivity. Therefore the method of the invention is preferably performed by growing cells transformed with a recombinant vector according to the second aspect of the invention (such as yEGFP-4443 or yEGFP-444), incubating the cells with the agent which putatively causes DNA damage for a predetermined time and monitoring the expression of the light emitting reporter protein directly from a sample of the cells.

When whole cells are used they are preferably contained in low fluorescence growth medium. This can obviate the need to wash the cells before measurements are made and therefore reduce the number of steps in the method further. For instance, preferred yeast according to the third aspect of the invention may be grown in F1 medium (described in Walmsley et al. (1983) Mol. Gen. Genet. 192 p361–365).

According to a preferred embodiment of the method of the invention FF 18984 cells may be transformed with yEGFP-444 and grown in F1 medium. A putative DNA damaging agent (e.g. a food additive or potential medicament or an agent contained within a water sample or effluent sample) may then be added to the F1 medium containing the cells. The cells are then allowed to grow for a defined period of time after which a sample of the cells is removed and fluorescence measured therefrom. This measurement may be effected by estimating the cell concentration and fluorescence in the sample using nephelometry (light scattering).

For example, cells can be illuminated at 600 nm and the scattered light (at 600 nm) estimated at 90 degrees to the incident beam. The light emitted by GFP can be measured by excitation at 495 nm and fluorescent light emitted at 518 nm measured at 90 degrees to the incident beam. Both measurements may be made in a single cuvette. A normalised GFP light emission is calculated by dividing the GFP fluorescence value by the whole cell light scattering value (at 600 nm). This embodiment of the invention has the advantage that it may be easily carried out with a minimum of steps (i.e an incubation period followed by direct fluorescence measurement).

The method of the invention should ideally employ sensitive fluorimeters and reduce light scattering in order that light emission can be accurately measured from the reporter protein. We have found that sensitivity can be improved by using a 495 nm filter which is introduced between the sample chamber and the emission-detector of the fluorimeter. Such a filter further reduces the impact of light scattering and improves the sensitivity of the method when samples containing whole cells are used.

The present invention will now be described, by way of examples, with reference to the accompanying drawings in which.

EXAMPLE 1

1.1 METHODS

1.1.1 Preparation of DNA coding for the RAD54 promoter

Figure 2:
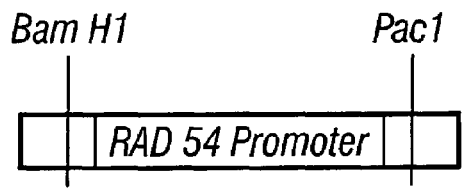
FIG. 2 is a schematic representation of DNA coding for the RAD54 promoter prepared by PCR amplification as described in 1.1 of Example 1.

A DNA fragment was prepared which contained the promoter region of the RAD54 gene and is schematically represented in FIG. 2.

The RAD54 gene is on Chromosome VII of the yeast *Saccharomyces cerevisiae*. The sequence of the entire genome of *Saccharomyces cerevisiae* is available on public databases. For instance the *Saccharomyces cerevisiae* genome database may be accessed by the World Wide Webb at many sites such as http://genome-www.stanford.edu/. The relevant region of Chromosome VII which contains the RAD54 gene and regulatory element of interest spans bases 193710–198141.

The DNA fragment containing the promoter region of the RAD54 gene was prepared by Polymerase Chain Reaction (PCR) amplification of the upstream non-coding region of RAD54 between the RAD54 start codon (ATG) and next gene (SUT1). This region spans 1729 base pairs and contains all sequences known to be involved in RAD54 regulation (i.e. the regulatory element). This region is encoded by SEQ ID NO 1.

The PCR amplification was carried out using two PCR primers called BAM54 and 54PAC which are identified as sequence listings SEQ ID NO 2 and SEQ ID NO 3 respectively.

BAM54 comprises the following 31 bases:

5'cctccggatccgacatacgatgacctcaatg 3'

BAM54 (SEQ ID NO:2) was designed to contain the bases ggatcc to ensure that the PCR product contained a BamH1 restriction site and the bases gacatacgatgacctcaatg which correspond to (SEQ ID NO:7) to the first 20 bases after the SUT1 gene in order that BAM54 may bind to the desired DNA fragment. The 5' bases cctcc were added to ensure BamH1 could cut at the introduced site.

54PAC (SEQ ID NO:3) comprises the following 44 bases:

5'cctccgttaattaacatcagttataaggaaatatatatggtacc 3'

54PAC was designed to contain the bases ttaattaa to ensure that the PCR product contained a Pac1 restriction site, the bases cagttataaggaaatatatatggtacc (SEQ ID NO:8) correspond to the first 27 upstream bases of the RAD54 gene in order that 54PAC may bind to the desired DNA fragment and the 5' bases cctcg were added to ensure Pac1 could cut at the introduced site. The primer 54PAC forms the antisense strand of the amplified fragment and therefore the bases in 54PAC that ultimately code for a reporter protein of a DNA molecule according to the first aspect of the invention are "antisense codons" such that the bases cat were introduced to add the amino acid methionine which acts as a start codon in a recombinant vector of the second aspect of the invention and the bases cctccgttaattaacat(SEQ ID NO: 9) are also "antisense" coding sequence.

Figure 1:
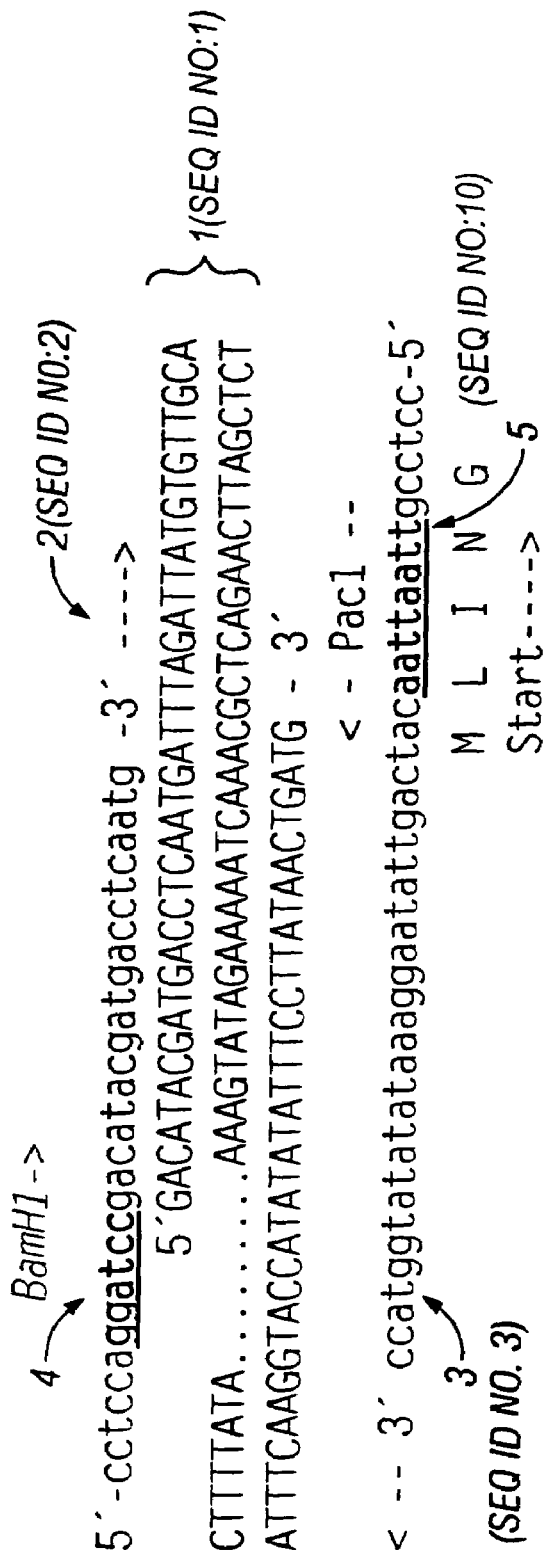
FIG. 1 is a schematic representation of DNA coding for the RAD54 promoter showing where the PCR primers used in Example 1 bind to the DNA.

FIG. 1 shows a schematic representation of the 5' and 3' portions of the DNA fragment (1) (SEQ ID NO:1) which was PCR amplified and illustrates where primers BAM54 (2) (SEQ ID NO:2) and 54PAC (3) (SEQ ID NO: 3) bind to the fragment. FIG. 1 further shows the BamH1 restriction site (4) and the Pac1 site (5) which were introduced into the PCR amplified fragment (1). The transcription start, the codons for the first 5 amino acids of a protein expressed from the RAD54 promoter and the direction of transcription are also shown.

Following PCR amplification the DNA coding for the RAD54 promoter was inserted into a PFA vector to form a recombinant vector of the invention (see 1.3).

1.1.2 The PFA KANMX3GFP construct

A PFA vector was used in the construction of recombinant vectors according to the invention. The PFA plasmid series has been previously published (Wach et al. (1994) Yeast 10 p 1793–1808).

Figure 3:
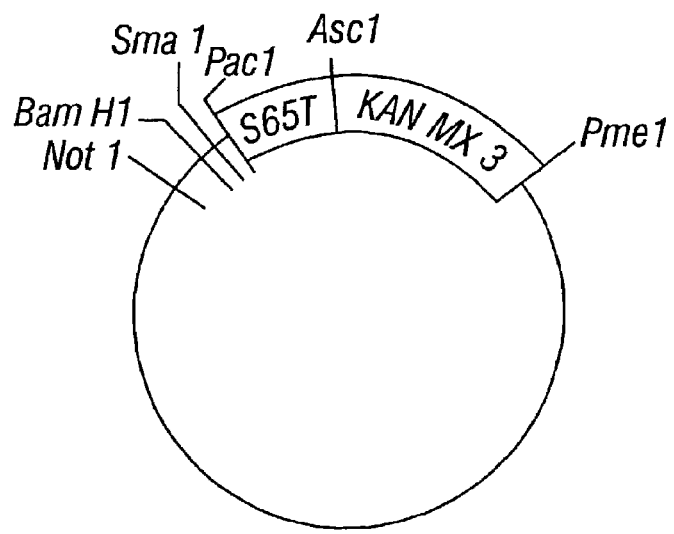
FIG. 3 is a schematic representation of the PFA KANMX3GFP construct used in Example 1 in the preparation of DNA molecules of the invention.

A plasmid PFA KANMX3GFP was derived from the known plasmid PFA KANMX3 (shown in FIG. 1B, page 1797 of Wach et al.) In the plasmid used by the inventors the lacz sequences of PFA KANMX3 were replaced by GFP sequences to form PFA KANMX3GFP, The sequence of PFA KANMX3GFP is attached as SEQ ID NO 4. (see FIG. 3)

PFA KANMX3GFP contains a DNA sequence coding for the S65T derivative of GFP which has a Pac1 site just after the transcription start codon of the GFP gene. S65T was inserted into the vector as a Pac1/Asc1 fragment. PFA KANMX3GFP also contains DNA (2689 bp) encoding for a gene capable of conferring kanamycin resistance.

Figure 4:
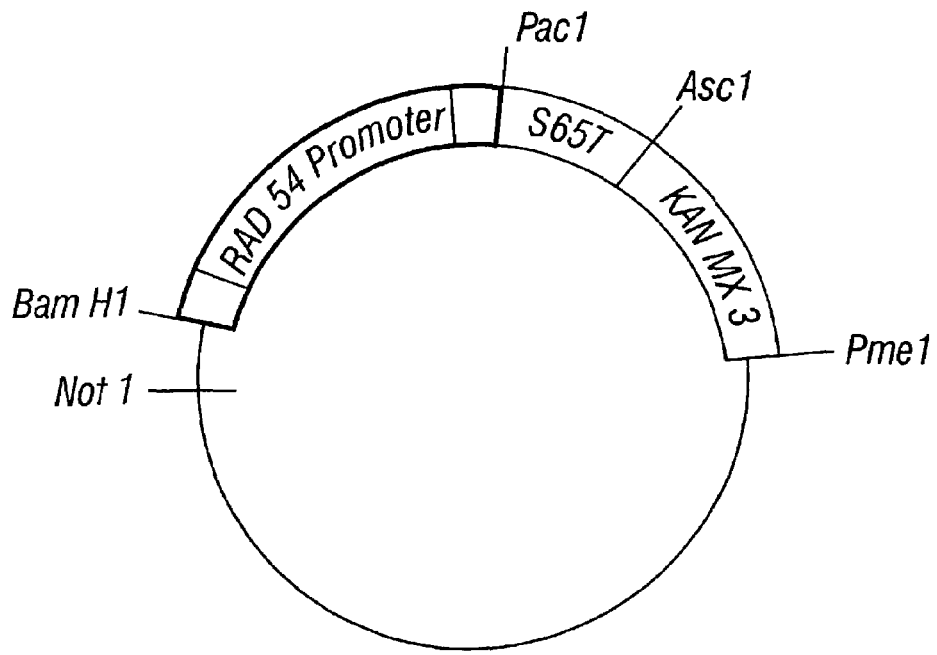
FIG. 4 is a schematic representation of the PFA KANMX3GFP-RAD54 recombinant vector of Example 1 which incorporates a DNA molecule of the invention.
Figure 5:
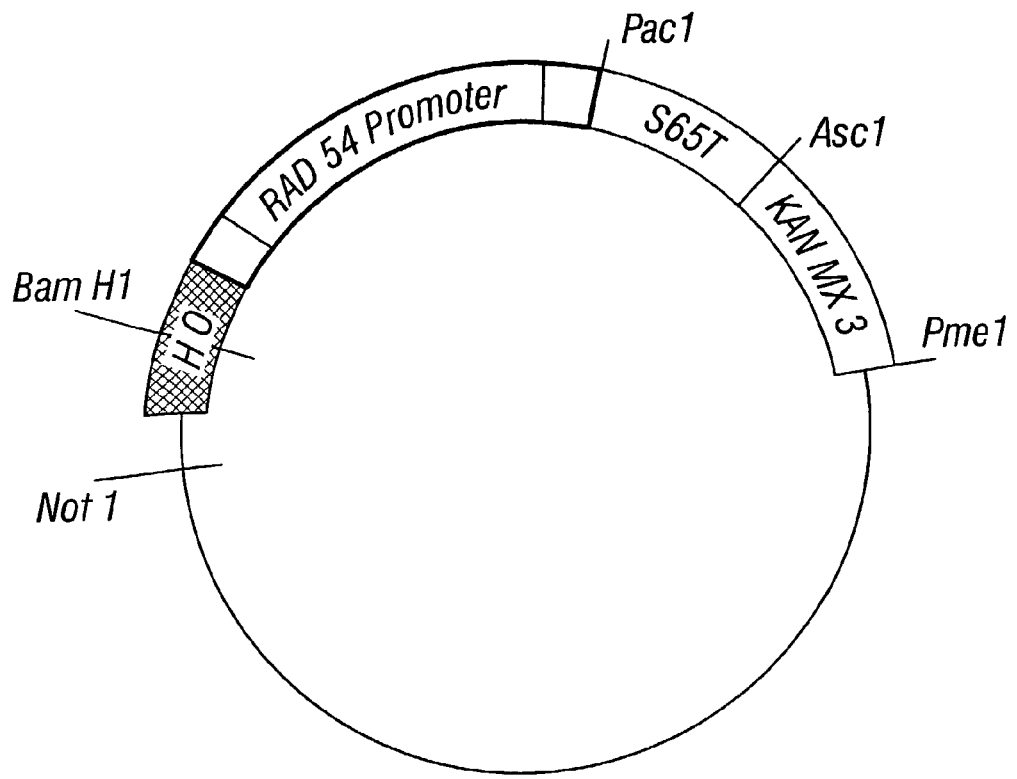
FIG. 5 is a schematic representation of the pWDH443 recombinant vector of Example 1 which incorporates a DNA molecule of the invention.

1.1.3 The KANMX3GFP-RAD54 construct (see FIG. 4)

The DNA coding for the RAD54 promoter (see 1.1) and PFA KANMX3GFP (see 1.2) were treated with the restriction enzymes BamH1 and Pac1. The KANMX3GFP-RAD54 construct was then made by uniquely ligating the DNA coding for the RAD54 promoter (with BamH1 and Pac1 sticky ends) into the linearised PFA KANMX3GFP between the unique BamH1 and Pac1 site adjacent to the S65T coding sequence. To ease cloning PFA KANMX3GFP was also treated with Sma1. The Sma1 site in PFA KANMX3GFP lies between BamH1 and Pac1, therefore the Sma1 treatment prevented recircularisation of the vector. The Pac1 site is "in-frame" such that the S65T gene may be transcribed.

1.1.4 The pWDH443 construct

The KANMX3GFP-RAD54 construct was cut at the unique BamH1 site, then treated with DNA polymerase (polI) and calf intestinal phosphatase to produce blunt and un-self ligatable ends. A Dra1 fragment (see SEQ ID NO 5) of the HO gene was then ligated between the blunt ends of the treated KANMX31-RAD54 construct to form the pWDH443 construct.

The HO gene is found on Chromosome IV of the yeast chromosome and sequences are held in the *Saccharomyces cerevisiae* genome database, which is in the public domain. The database may be accessed by the World Wide Web at many sites. For example at http://genome-www.stanford.edu/

The Dra1 fragment of the HO gene contains a BamH1 site at bases 711–716 of SEQ ID NO 5 and was employed to promote integration of the construct into the yeast genome by the known technique of homologous integration.

The pWDH443 construct can be cut with BamH1 and used to transform yeast (Y485/486) with G418 selection (a derivative of kanamycin). Transformation was done using the known Lithium acetate procedure (see http://www.u-manitoba.ca/faculties/medicine/human_genetics/gietz/Trafo.html).

The pWDH443 construct integrates into the yeast genome at the HO locus. pWDH443 is a preferred recombinant vector according to the second aspect of the invention and cells transformed with pWDH443 are preferred cells according to the third aspect of the invention.

Figure 6:
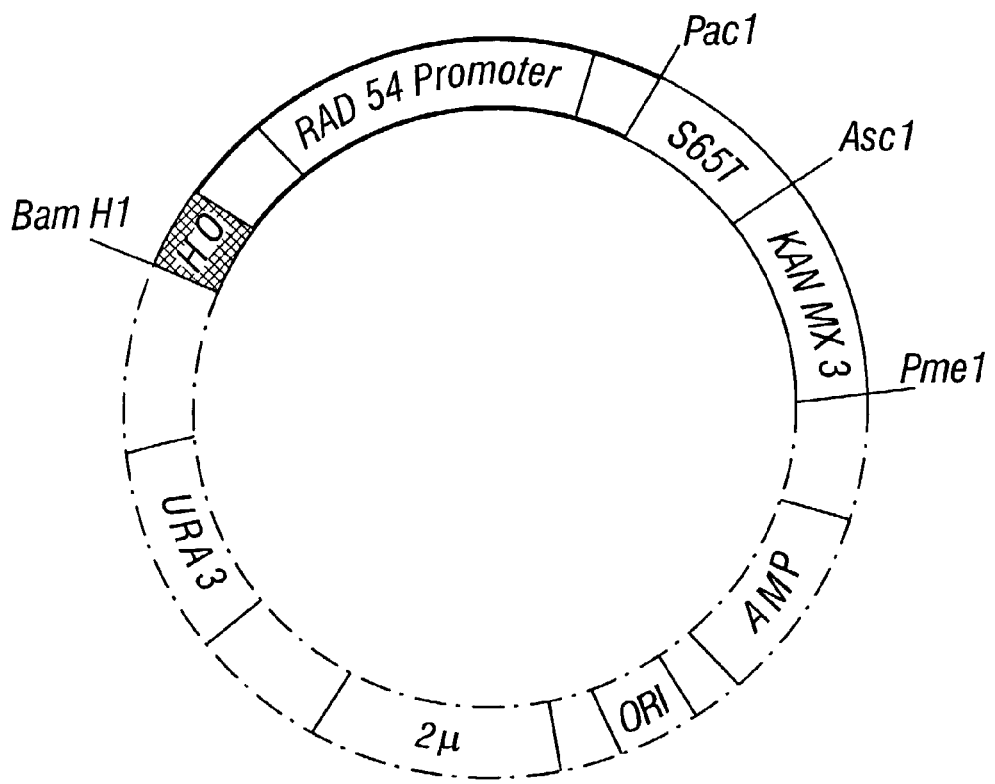
FIG. 6 is a schematic representation of the pWDH444 recombinant vector of Example 1 which incorporates a DNA molecule of the invention.

1.1.5 The pWDH444 construct (see FIG. 6)

The pWDH444 construct was then developed (by manipulation of pWDH443) such that the construct was capable of replication inside a yeast host to be present as multicopies. To do this a DNA fragment (blunt at one end and BamH1 cut at the other) containing sequences encoding for cis-acting replication factors from the naturally occurring yeast 2μ plasmid, yeast URA3 gene (uracil prototrophy) and bacterial plasmid pBR322 sequences conferring replicative ability (ORI) and ampicillin resistance (AMPr) to the construct (when maintained in *E. coli*) were ligated into pWDH443 cut with BamH1 and PmeI. This cut removed a fragment of pWDH443 which contained a Not1 site. The ligation mix was cut with Not1 prior to transformation to prevent recircularisation of pWDH443. The BamH1 site within the HO fragment (see above) and the HO fragment is therefore truncated in the pWDH444.

The 2μ plasmid fragment contained sequences corresponding to the yeast 2μ origin, URA3 gene, pBR322 ORI sequence and Ampicillin resistance are found as a contiguous fragment in several plasmids. (For instance the shuttle vector named Yep420.) The 2μ plasmid fragment used by the inventors corresponds precisely to the large HindIII/BamH1 fragment released from the plasmid pRDK249, described in the Journal Biological Chemistry, Volume 266, p14049, FIG. 1 (1991) in the article by Johnson, A. W. and Kolodner, R. D. Specifically, the plasmid was first cut with HindIII, then treated with DNA polymerase I to produce a blunt end. The plasmid was then treated with BamH1 producing a fragment blunt at one end and with a BamH1 end at the other. This fragment was purified by gel electrophoresis.

The pWDH444 construct was used to transform yeast (as described for pWDH443) selecting for either uracil prototrophy (URA3) or G418 (kanamycin) resistance and was capable of autonomous replication with the yeast. pWDH444 is a preferred recombinant vector according to the second aspect of the invention and cells transformed with pWDH444 are preferred cells according to the third aspect of the invention.

1.2. Fluorescence Determination Experiments

Light emitted by GFP at 511 nm (after excitation at 488 nm) from yeast cells transformed with pWDH443 and pWDH444 and expressing GFP was measured in a fluorimeter in the absence (controls) or presence of compounds known to induce DNA damage such as Methyl Methane Sulphonate (MMS). Samples were assayed as whole cells or as cell extracts.

1.2.1. Strains and Growth Conditions

Yeast strains Y485 and Y486 in haploid form or Y485/486 in diploid form were in this Example (see above).

The media YP plus 2% glucose (YPD) and synthetic media plus 2% glucose (SD) were prepared as described in Kaiser et al. (1994) (Methods in Yeast Genetics. Cold Spring Harbor Laboratory Course Manual, N.Y.: Cold Spring Harbor Press, Cold Spring Harbor Laboratory, NY, N.Y.).

1.2.2. Fluorescence Assays

A stationary phase culture of cells grown in SD medium was used as the inoculum source. Aliquots (30 μl) of cells were inoculated into 3 ml of SD in 15 ml test tubes. Half of the tubes were then supplemented with 0.01% MMS (the remaining tubes left as controls). The tubes were incubated at 25° C. for 16 h on an orbital shaker at 120 rpm, then transferred to an ice-box whilst maintaining agitation. The cells were then transferred to 1.5 ml eppendorf tubes, harvested by centrifugation (10 s), washed twice in sterile distilled water, and resuspended in 250 μl extraction buffer.

For whole cell fluorescent measurements, the washed cells were transferred directly to cuvettes containing 2.75 ml sterile distilled water.

For cell extract studies, 100μl of 400–600nm diameter glass beads were added to the tubes of cells which were then placed in a BIO 101 Fastprep FP120 to mechanically disrupt the cells. Following centrifugation for 30 s, the supernatant was transferred to a clean tube. The pellet of beads was washed in a further 250 μl of extraction buffer and this was added to the supernatant from the previous extraction. 200 μl of the pooled extract in 300 μl of water was then transferred to a cuvette.

Fluorescence measurements were performed with a Perkin Elmer LS50 Fluorescence Spectrometer. The excitation and emission wavelengths were set to 488nm and 511 nm, respectively, with a slit width of 10 nm. To correct for variations in cell number/protein extraction efficiency, light absorption was recorded for each cuvette at either 600 nm (for whole cells) or 280 nm (for extracts). The fluorescence values obtained from the fluorometer were then divided by the absorption readings to give the "brightness value", an arbitrary unit independent of sample concentration. Other data handling details are dealt with either in the text or in the

1.2.3 Results

For pWDH443 transformed yeast, both mating types (Y485 and Y486) and the diploid (Y485/486) showed statistically significant increases in fluorescence when exposed to 0.002% and 0.01% MMS.

Figure 7:
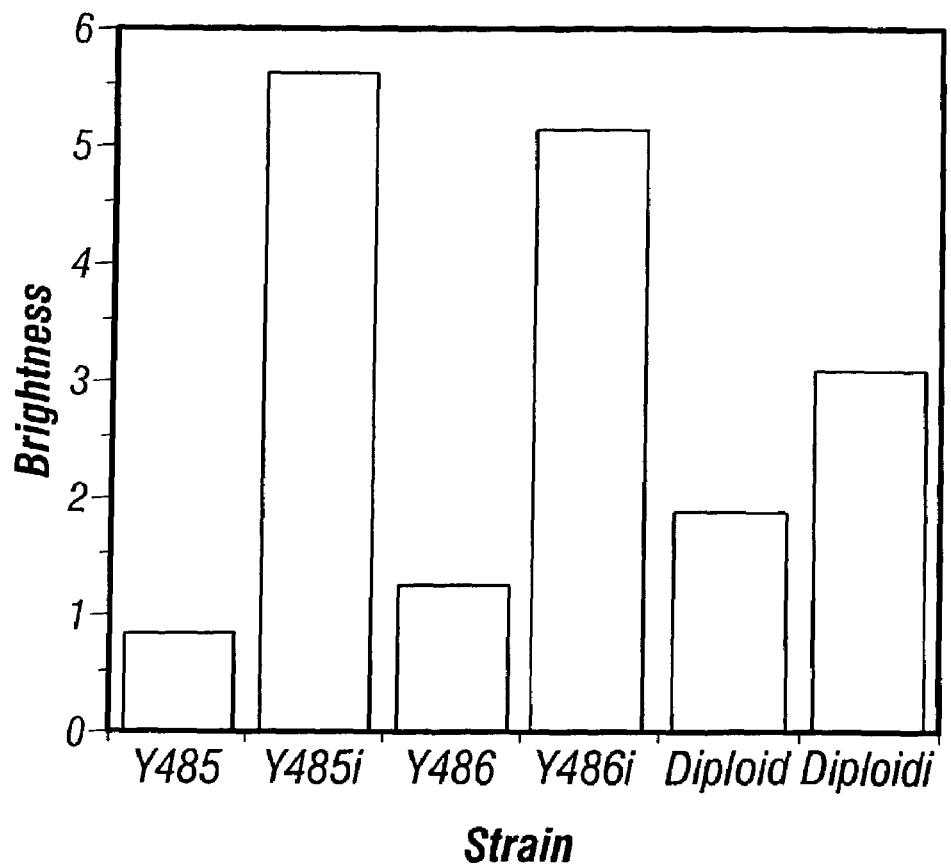
FIG. 7 is a graph illustrating an increase in fluorescence occurs in cells according to the third aspect of the invention when the cells are exposed to a DNA damaging agent.

As shown in FIG. 7, pWDH443 transformed yeast (Y485, Y486 and diploid [Y485/486]) also showed an increase in brightness in the presence of the DNA damaging agent MMS (Y485i, Y486i and Diploidi) relative to untransformed cells also exposed to MMS (Y485, Y486 and Diploid).

Figure 9:
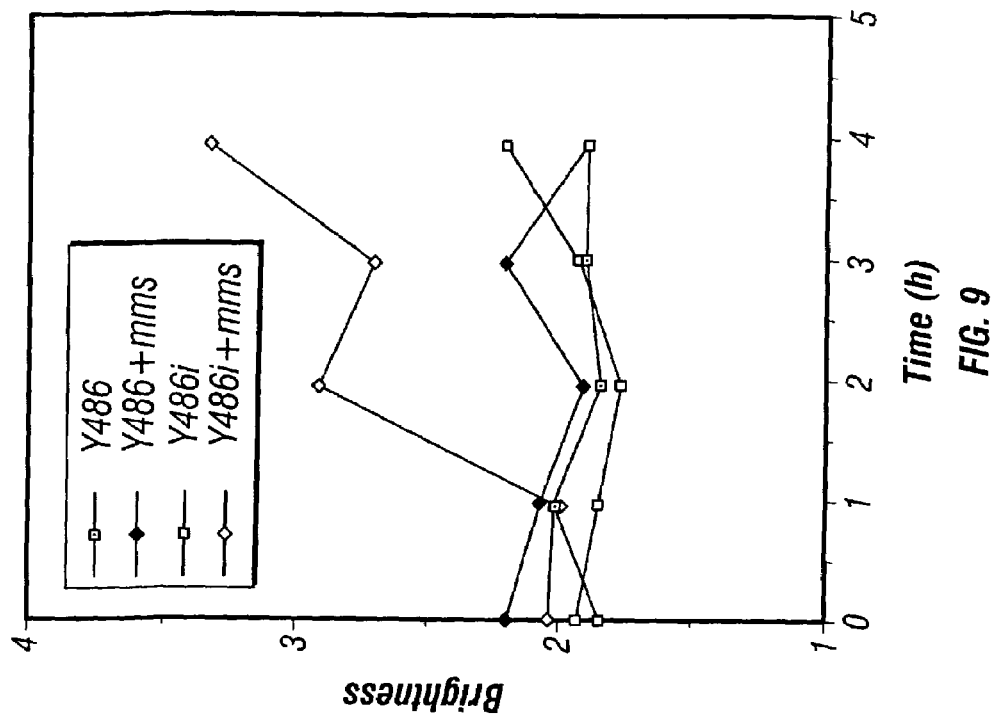
FIG. 9 is a graph illustrating the time course of the induction of brightness by a DNA damaging agent for a cell transformed with pWDH443.
Figure 8:
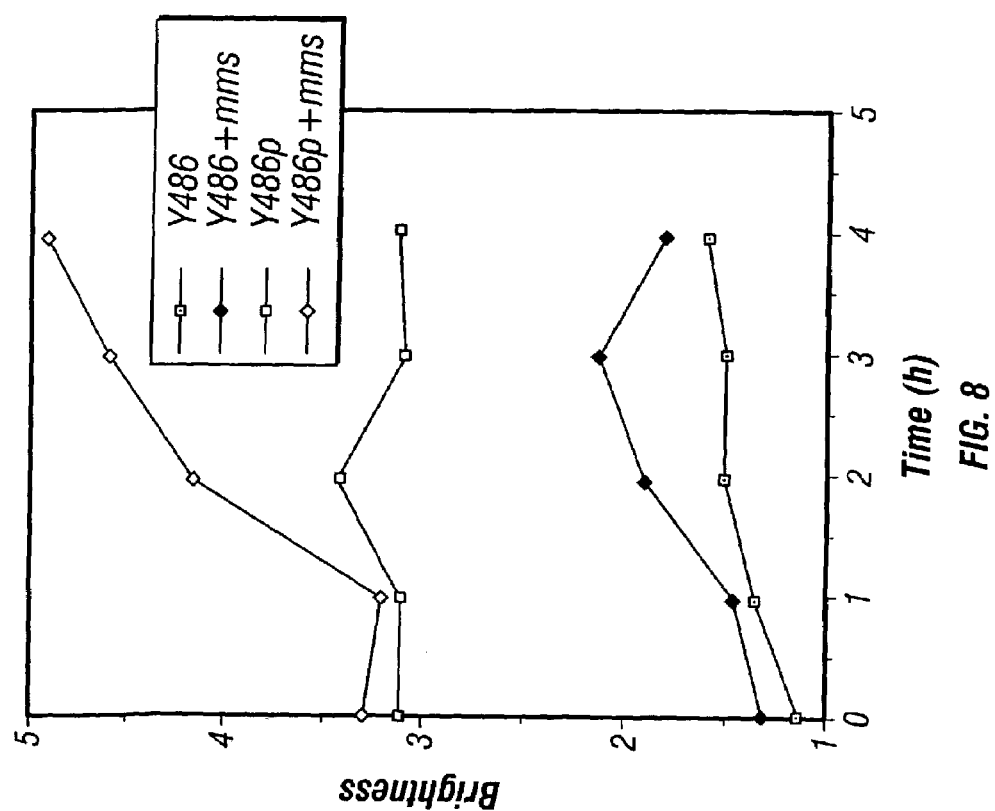
FIG. 8 is a graph illustrating the time course of the induction of brightness by a DNA damaging agent for a cell transformed with pWDH444.

Fluorescence began to increase one hour after induction with 0.05% MMS. FIG. 8 and FIG. 9 show time courses of the induction of brightness by MMS in the haploid yeast strain Y486 transformed with pWDH444 (Y486p+mms) or pWDH443 (Y486i+mms) respectively. The effect of MMS on untransformed cells (Y486+mms) and brightness in untreated cells (Y486, Y486p and Y486i) is also shown.

Figure 10:
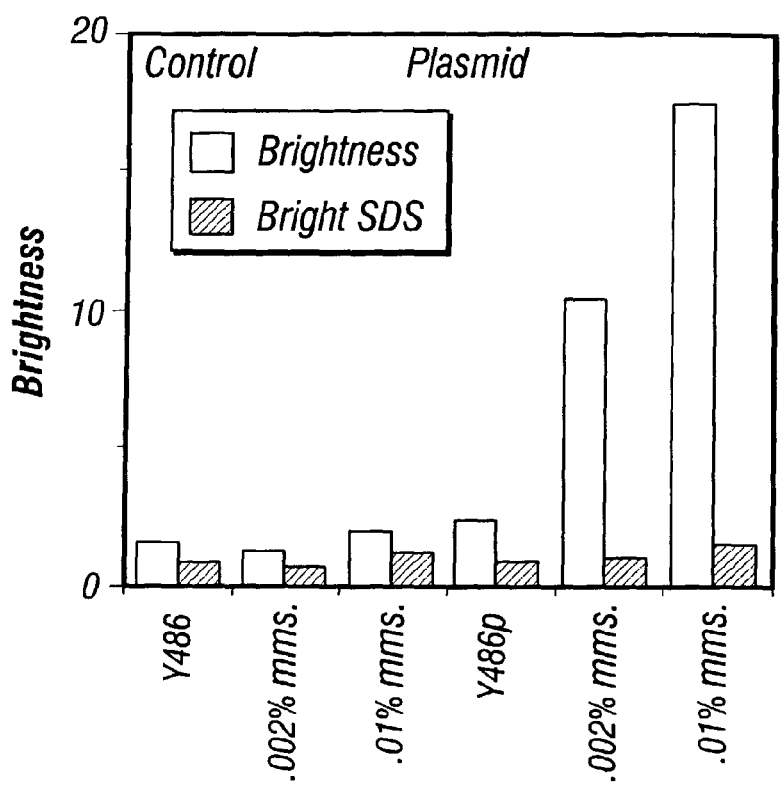
FIG. 10 is a graph illustrating the effect of differing concentrations of a DNA damaging agent on cell extract brightness by a DNA damaging agent for extracts from a cell transformed with pWDH444.

FIG. 10 illustrates that 0.02% and 0.05% MMS causes an increase in fluorescence in the haploid yeast strain Y486 that has been transfected with pWDH444 (Y86p) but has no significant effect in untransformed cells (Y486). SDS was included as a control to abolish fluorescence from GFP.

Protein extracts from untransformed yeast cells and yeast cells transformed with both pWDH443 and pWDH444 were used in a Western blot analysis using anti-GFP antibody. GFP was not detected in untransformed cells and was only detected at low levels in uninduced transformed cells. However when yeast cells transformed with pWDH443 or pWDH444 were induced with MMS there was a considerable increase in GFP antibody binding. This increase was proportional to the measured fluorescence and therefore confirmed that the increase in fluorescence was due to DNA damage inducing the RAD54 promoter and subsequently causing GFP expression.

These data illustrate that yeast transformed with pWDH443 and pWDH444 emit increased fluorescence (at 511 nm) in the presence of a DNA damaging agent. Accordingly pWDH443 and pWDH444 are highly preferred recombinant vectors according to the second aspect of the present invention and yeast transformed with pWDH443 and pWDH444 are highly preferred cells according to the third aspect of the invention. These transformed yeast cells are highly suited to be used according to the method of the fourth aspect of the invention although it will be appreciated that alternative recombinant vectors may be constructed according to the second aspect of the present invention and cells transformed with such alternative recombinant vectors will fall within the scope of the present invention.

Cells transformed with pWDH443 and pWDH444 may be used in a method according to the fourth aspect of the present invention as a means of screening compounds, such as candidate medicaments, food additives or cosmetics, to assess whether it is safe to expose a living organism, particularly people, to such compounds or the cells may be used to detect whether water supplies are contaminated by DNA damaging agents or agents that potentiate DNA damage.

EXAMPLE 2

Recombinant vector yEGFP-444 was formed and used to transform yeast cells which expressed YEGFP in response to a DNA damaging agent (MMS).

2.1. METHODS 2.1.1. Strains and Growth Conditions

Yeast strain used in this Example:

(i) FF18984 (MATα leu2-3,112 ura3-52 lys2-I his7-I)

(ii) YLR030wα (MATα his3Δ200 ura3-52)

The media used was the same as described in 1.2.1.

2.1.2 DNA constructs

Figure 12:
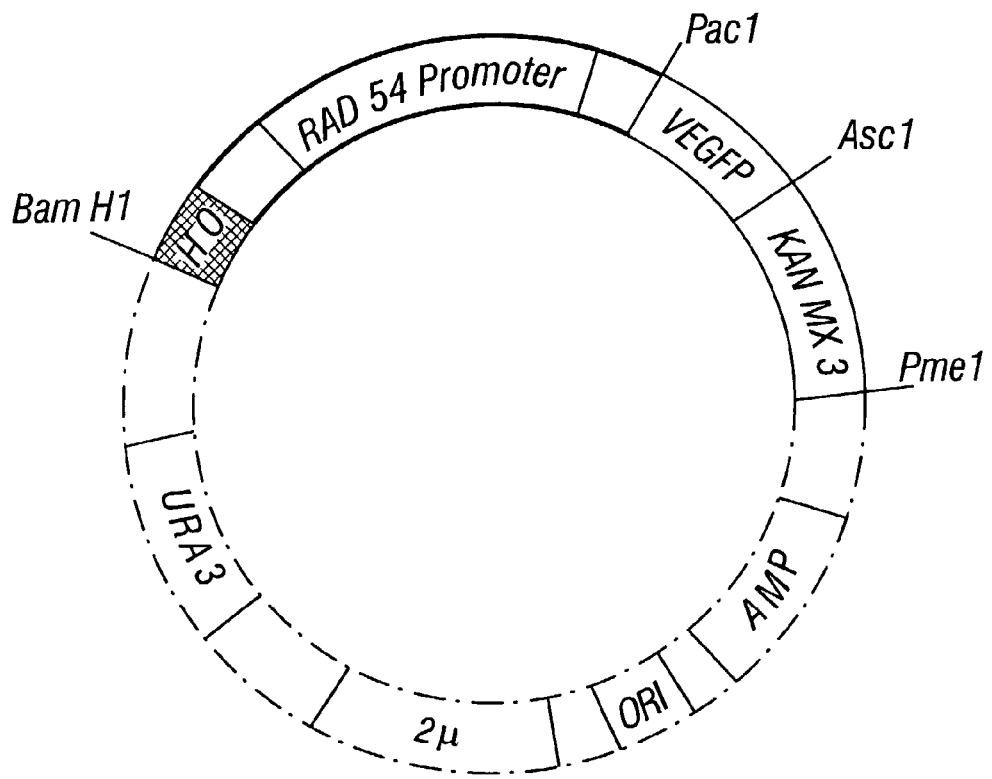
FIG. 12 is a schematic representation of the yEGFP-444 recombinant vector of Example 2 which incorporates a DNA molecule of the invention.

The modular design of pWDH444 (see Example 1) allowed simple replacement of the S65T derivative of GFP with the YEGFP gene (Cormack et al, 1997 supra) to form preferred recombinant vector yEGFP-444 (see FIGS. 12).

YEGFP was PCR amplified using primers that added flanking Pac1 and Asc1 restriction enzyme sites to yield the PCR product of SEQ ID NO. 6. This PCR product was then cut with Pac1 and Asc1.

The S65T GFP gene was released from pWDH444 by cutting with Pac1 and Asc1, and gel electrophoresis was used to purify the remaining vector fragment (i.e. the large fragment).

The larger Pac1 and Asc1 fragment of the PCR product was then ligated into the large fragment of pWDH444 to form yEGFP-444.

2.2 FLUORESCENCE DETERMINATION EXPERIMENTS 2.2.1 Fluorescence Assays

The assessment of GFP fluorescence in whole cells was performed essentially as described in 1.2 (above).

2.2.2 Results

Light output from cells transformed with plasmid yEGFP-444 was even greater than from those transformed with pWDH443 or pWDH444. In fact, Table 1 illustrates that light output more than doubled from FF18984 transformed with yEGFP-444 relative to FF 18984 transformed with pWDH444.

TABLE 1

Comparison of fluorescence output from yEGFP-444 and pWDH444.

| Recombinant Vector | Brightness (BU) + MMS | Brightness (BU) − MMS |
|---|---|---|
| yEGFP-444 | 100 | 45 |
|  | 97 | 41 |
|  | 93 | 47 |
|  | average = 96.7 | average = 44.3 |
| pWDH444 | 45 | 27 |
|  | 54 | 29 |
|  | 48 | 26 |
|  | average = 49 | average = 27.3 |

We have found that pWDH443 and pWDH444 is suitable for use according to the method of the invention, when light production (in response to DNA damage) is measured from cell extracts derived from cells according to the fourth aspect of the invention (in order that a good signal to noise ratio is achieved). pWDH443 and pWDH444 are of limited use for whole cell measurements partly as a consequence of light scattering. There is only a narrow difference between the excitation (475–495 nM) and emission (approximately 512 nM) wavelengths used in GFP assessment. Using yEGFP-444, together with a sensitive spectrophotometer, it became possible to see the GFP signal as a correctly positioned shoulder on the fluorescence scan.

Figure 13:
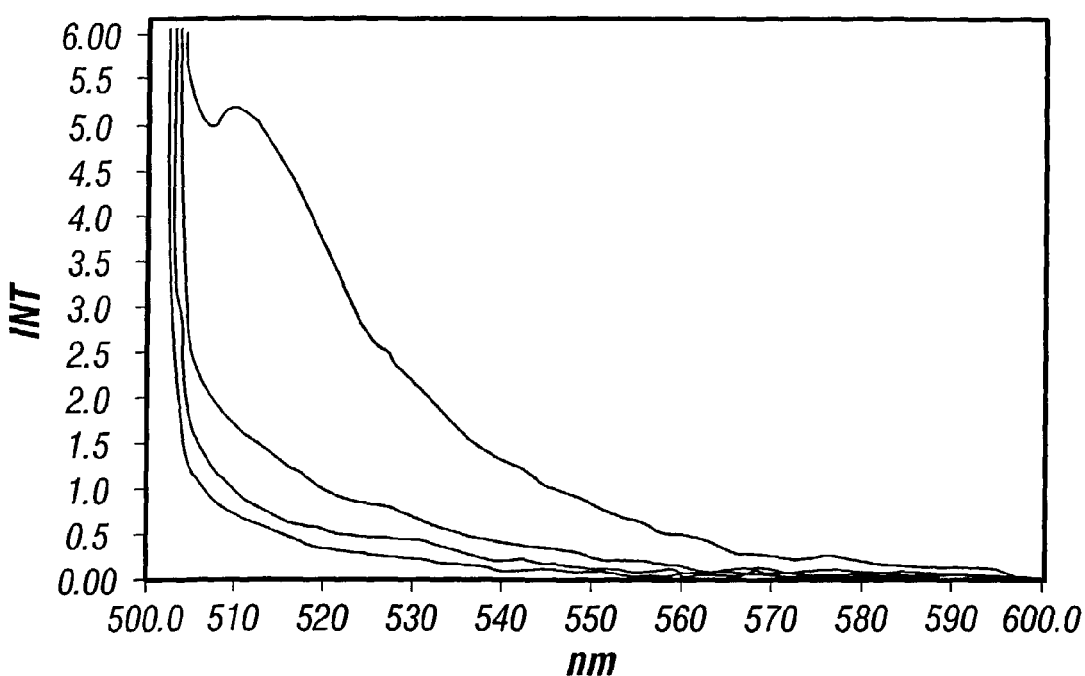
FIG. 13 is a graph illustrating emission spectra of yeast cells untransformed and transformed cells with yEGFP-444 −/+0.01% MMS.

FIG. 13 illustrates emission spectra (excitation at 488 nm) from 0.2 OD600 units of FF18984 cells untransformed and transformed cells with yEGFP-444 −/+0.01% MMS. Cells were twice washed in sterile water before resuspending in 1× TE and further dilution. The lowest spectrum represents the fluorescence measured from untransformed cells with an MMS challenge and the next shows the same cells without MMS. The middle spectrum represents FF18984 cells transformed with the yEGFP-444 construct without an MMS challenge, whilst the upper spectrum shows the result of an MMS insult on the same transformed cells.

Other experiments were performed to refine the assay. To further reduce the impact of light scattering, a 495 nm filter was introduced between the sample chamber and the emission-detector. This greatly enhanced the sensitivity of the instrument such that the difference between uninduced and induced cells was the same as that obtained with cell extracts. Furthermore when cells were grown in F1 medium (supra), it was not necessary to wash cell samples before transferring to the spectrophotometer.

We also performed experiments to demonstrate that the light output from cells according to the third aspect of the invention was specific to DNA damage and not a cell cycle phenotype. These experiments involved exposing transformed cells to hydroxyurea and nocodazole which can delay mitosis in different ways. Hydroxyurea interferes with DNA synthesis at two levels: it inhibits ribonucleotide reductase, so limiting the supply of precursors for DNA synthesis, and it inhibits DNA ligase, an enzyme responsible for repairing nicks (single strand breaks) in the DNA backbone. In contrast nocodazole inhibits microtubule formation and thus primarily arrests cell growth by preventing the normal segregation of chromosomes during mitosis. At concentrations of these two chemicals that inhibited cell growth to a similar extent to our MMS treatment regime, there was no detectable induction of the GFP reporter gene which demonstrates that light emission was not related to the cell cycle and was induced by DNA damage inducing activation of the RAD54 promoter.

EXAMPLE 3

Figure 11:
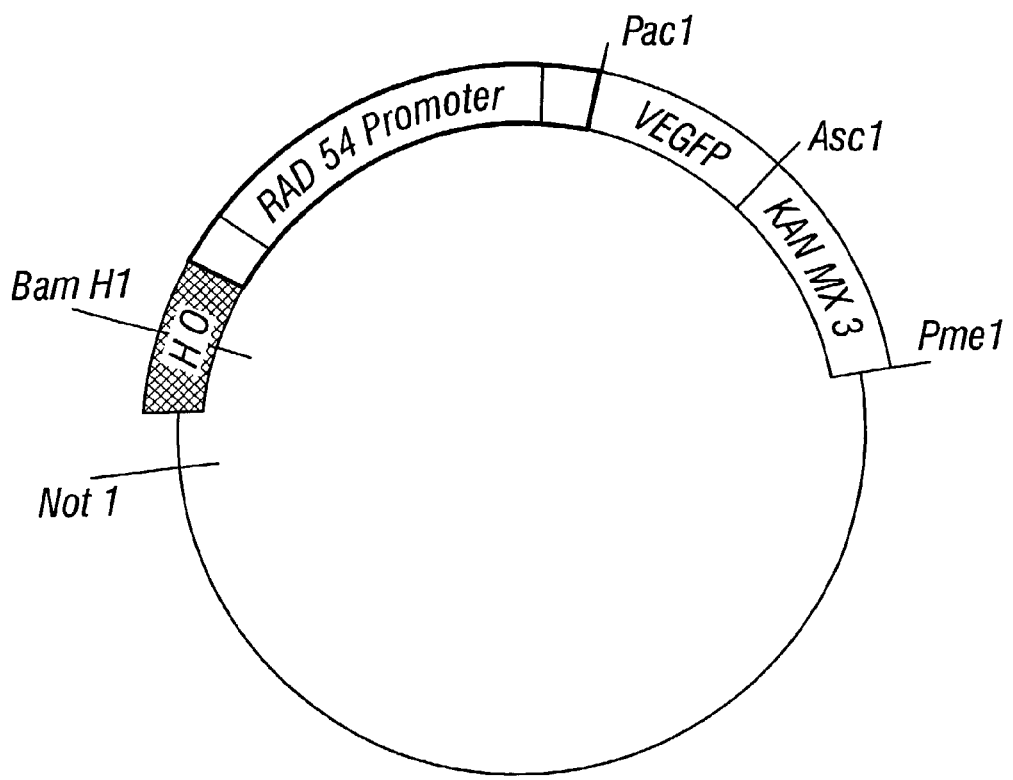
FIG. 11 is a schematic representation of the yEGFP-443 recombinant vector of Example 3 which incorporates a DNA molecule of the invention.

The modular design of pWDH443 (see Example 1) may also be exploited to allow simple replacement of the S65T derivative of GFP with the YEGFP gene to form preferred recombinant vector yEGFP-443 (see FIG. 11).

The method described in Example 2 may be followed to produce yEGFP-443 with the exception that pWDH443 was used instead of pWDH444.

Cells transformed with yEGFP-443 are also useful for use according to the method of the invention.

Cells transformed with yEGFP-444 and pWDH444 are particularly useful for detecting DNA damage without needing to disrupt cells to form an extract for assaying. The combination of the YEGFP gene, a sensitive host strain (e.g. FF 18984), a low fluorescence medium (e.g. F1) and optimally the limitation of light scattering in the detecting device (e.g. using a 495 nm filter) allows a shift away from the time consuming and complex assay of cell extracts to direct measurements of samples containing whole cells.

The invention claimed is:

1. A method of detecting the presence of an agent that causes or potentiates DNA damage comprising:
   a) subjecting a cell to the agent, wherein the cell contains a recombinant vector comprising a DNA vector and a recombinant DNA molecule comprising an RNR regulatory element selected from the group consisting of regulatory elements from RNR1, RNR2, or RNR3 genes, wherein said regulatory element is operatively linked to a DNA sequence that encodes a Green Fluorescent Protein or a light emitting derivative thereof, and
   b) monitoring the expression of the Green Fluorescent Protein from the cell, wherein an increase in the expression in the presence of the agent indicates that the agent causes or potentiates DNA damage.

2. The method according to claim 1, wherein the agent is further screened to assess whether it is safe to expose a living organism to the agent.

3. The method according to claim 1 wherein the agent is a candidate medicament, food additive or cosmetic.

4. The method according to claim 1 wherein the agent is a contaminant of water supplies.

5. The method according to claim 1 wherein the agent is a contaminant of industrial effluents.

6. The method according to claim 1 wherein the expression of Green Fluorescent Protein is measured from a whole cell.

7. A method of detecting the presence of an agent that causes or potentiates DNA damage comprising:
   a) growing cells transformed with a recombinant vector comprising a DNA vector and a recombinant DNA molecule comprising an RNR regulatory element selected from the group consisting of regulatory elements from RNR1, RNR2, or RNR3 genes, wherein said regulatory element is operatively linked to a DNA sequence that encodes a Green Fluorescent Protein or a light emitting derivative thereof,
   b) incubating the cells with the agent for a predetermined time, and
   c) monitoring the expression of the Green Fluorescent Protein directly from a sample of the cells, wherein an increase in the expression in the presence of the agent indicates that the agent causes or potentiates DNA damage.

8. The method according to claim 1 wherein the cell is grown in a low fluorescence growth medium.

9. The method according to claim 8 wherein the low fluorescence growth medium is F1 medium.

10. The method according to claim 1 wherein the expression of Green Fluorescent Protein is measured from an extract of the cell.

* * * * *

UNITED STATES PATENT AND TRADEMARK OFFICE
CERTIFICATE OF CORRECTION

PATENT NO. : 7,049,071 B2  Page 1 of 1
APPLICATION NO. : 10/244292
DATED : May 23, 2006
INVENTOR(S) : Walmsley et al.

It is certified that error appears in the above-identified patent and that said Letters Patent is hereby corrected as shown below:

On the Front Page, Col. 1, line 73 (Assignee Section), change "University of Manchester Institute of Science and Technology" to --Gentronix Limited--.

Signed and Sealed this

Twenty-seventh Day of November, 2007

JON W. DUDAS
*Director of the United States Patent and Trademark Office*